United States Patent
Duan et al.

(10) Patent No.: US 11,839,462 B2
(45) Date of Patent: Dec. 12, 2023

(54) GASTROINTESTINAL TRACT POSITIONING SWITCH, MANUFACTURE METHOD THEREOF AND SITE-SPECIFIC DELIVERY CAPSULE

(71) Applicant: Ankon Medical Technologies (Shanghai) Co., LTD., Shanghai (CN)

(72) Inventors: Xiaodong Duan, Pleasanton, CA (US); Hongjiao Song, Shanghai (CN)

(73) Assignee: ANKON MEDICAL TECHNOLOGIES (SHANGHAI) CO., LTD., Shanghai (CN)

( * ) Notice: Subject to any disclaimer, the term of this patent is extended or adjusted under 35 U.S.C. 154(b) by 642 days.

(21) Appl. No.: 16/729,346

(22) Filed: Dec. 28, 2019

(65) Prior Publication Data
US 2020/0205696 A1 Jul. 2, 2020

(30) Foreign Application Priority Data
Dec. 29, 2018 (CN) .......................... 201811644505.6

(51) Int. Cl.
| A61B 5/07 | (2006.01) |
| A61B 5/00 | (2006.01) |
| A61K 9/00 | (2006.01) |
| A61M 31/00 | (2006.01) |

(52) U.S. Cl.
CPC ............ *A61B 5/073* (2013.01); *A61B 5/4839* (2013.01); *A61B 5/6861* (2013.01); *A61K 9/0097* (2013.01); *A61M 31/002* (2013.01); *A61M 2210/1042* (2013.01)

(58) Field of Classification Search
CPC ..... A61B 5/073; A61B 5/4839; A61B 5/6861; A61B 5/14539; A61B 5/4238; A61B 5/4255; A61K 9/0097; A61K 47/32; A61K 47/36; A61K 9/48; A61M 31/002; A61M 2210/1042; A61J 3/07
See application file for complete search history.

(56) References Cited

U.S. PATENT DOCUMENTS

| 4,290,426 A * | 9/1981 | Luschen | A61K 9/0004 |
| | | | 424/428 |
| 5,899,876 A * | 5/1999 | Flower | A61N 1/30 |
| | | | 604/20 |
| 6,560,471 B1 * | 5/2003 | Heller | A61B 5/076 |
| | | | 600/347 |
| 2012/0289775 A1 * | 11/2012 | Murata | A61B 5/6861 |
| | | | 977/734 |
| 2014/0316222 A1 * | 10/2014 | Rabinovitz | A61B 5/0084 |
| | | | 600/302 |
| 2019/0167895 A1 * | 6/2019 | Dechelette | A61M 5/14566 |

* cited by examiner

*Primary Examiner* — James D Ponton
(74) *Attorney, Agent, or Firm* — Treasure IP Group, LLC

(57) ABSTRACT

The present invention provides a gastrointestinal tract positioning switch, a method of manufacturing the gastrointestinal tract positioning switch and a site-specific delivery capsule. The gastrointestinal tract positioning switch includes a base, a first electrode, a second electrode, a conductive device and a positioning film. The first electrode and the second electrode are spaced apart from each other and fixed on the base. The first electrode and the second electrode electrically connected to the conductive device respectively, and covered by the positioning film. Both the first electrode and the second electrode are an inert electrode, and can be exposed after dissolution or/and degradation of the positioning film in the stomach or intestine.

10 Claims, 4 Drawing Sheets

GASTROINTESTINAL TRACT POSITIONING SWITCH, MANUFACTURE METHOD THEREOF AND SITE-SPECIFIC DELIVERY CAPSULE

CROSS-REFERENCE OF RELATED APPLICATIONS

The application claims priority to Chinese Patent Application No. 201811644505.6 filed on Dec. 29, 2018, the content of which is incorporated by reference herein.

FIELD OF INVENTION

The present invention relates to the field of gastrointestinal tract positioning, and more particularly to a gastrointestinal tract positioning switch and manufacture method thereof and a site-specific delivery capsule.

BACKGROUND

At present, most gastrointestinal chronic diseases require oral delivery of drugs for long-term treatment, but because of a short stay of drugs in human body, and a large effect by gastric acid, the amount of drugs that reach the targeted site can be reduced or even none reach the targeted site, and consequently, the therapeutic effect is lowered. In addition, statistics show that about 40% of new drug candidates are eliminated not because of their unsatisfactory efficacy on human body, but because of poor experimental methods during the early development, which failed to accurately obtain the absorption characteristics of candidate drugs in different regions of the GI tract. Therefore, how to improve the local therapeutic effect in GI tract and study the absorption characteristics of drugs in different regions of GI tract has become the key to the treatment of gastrointestinal diseases and the development of new drugs.

As a typical Micro-Electro-Mechanical System (MEMS), the Site-Specific Delivery Capsule (SSDC) can provide an effective way to solve the above problems. SSDC can avoid the discomfort and even trauma to patients caused by traditional intubation and infusion methods, and does not interfere with the normal physiological state of GI tract. It improves the efficiency and accuracy of local absorption research and animal experiments of new drugs. Currently, the positioning technique of SSDC in GI tract adopts the methods as follows:

First, the positioning technique is with the assistance of external equipment. For example, the high frequency (HF) capsule developed by Hugeman et al. in Germany uses X-ray transmission for positioning in GI tract and uses radio frequency (RF) signals to trigger drug delivery. For example, the Enterion™ developed by Phaeton Research in the UK uses a high-frequency magnetic field to trigger the control mechanism and uses Gamma scintigraphy for drug location monitoring, which can carry 0.8 mL of drug. However, this method is not only complicated in the operation process, which is impossible for patients to use by themselves, but is also consumes large energy and has poor accuracy.

Second, the positioning technique uses pH sensor to determine the pH of GI tract. For example, the SSDC developed by Chongqing University uses a pH sensor to detect the pH of GI tract, and amplifies and filters the pH voltage signal, and then transmits the signal to a microprocessor which can determine whether to release drug according to the pH. However, the current pH sensors used in GI tract mainly can be glass electrode, antimony electrode, or hydrogen ion-sensitive field effect transistor. However, glass electrode is large and difficult to be integrated in capsule, antimony electrode has a limited life and is quite easy to be corroded, and hydrogen ion-sensitive field effect transistor has a poor stability and short service life.

SUMMARY OF THE INVENTION

The present invention provides a gastrointestinal tract positioning switch and manufacture method thereof and a site-specific delivery capsule. The GI tract positioning switch integrates positioning and triggering function, and does not need a large external instrument for positioning in GI tract. Therefore, SSDC becomes simple in operation and use, and realizes independent delivery of drug for patients. Moreover, it not only saves the space inside the capsule, provides ample space for drug delivery or/and sampling, but also reduces the cost of SSDC.

The present invention provides a gastrointestinal tract positioning switch, comprising a base, a first electrode, a second electrode, a conductive device and a positioning film, wherein the first electrode and the second electrode are spaced apart from each other and fixed on the base; wherein the first electrode and the second electrode are electrically connected to the conductive device respectively and covered by the positioning film; wherein both the first electrode and the second electrode are an inert electrode, and is exposed after dissolution or/and degradation of the positioning film in the stomach or intestine.

In one preferred embodiment, both the first electrode and the second electrode are an inert electrode made of inert conductive metal.

In one preferred embodiment, the first electrode and the second electrode are formed by applying an inert conductive metal coating on the base through sputtering coating process.

In one preferred embodiment, the conductive device is welded to the first electrode and the second electrode.

In another preferred embodiment, the conductive device is bonded to the first electrode and the second electrode through conductive adhesive.

In one preferred embodiment, the positioning film is formed by coating film-forming materials on the first electrode and the second electrode by a spray coating method or a dip coating method.

In one preferred embodiment, the base is made of an acrylonitrile-butadiene-styrene copolymer.

In one preferred embodiment, the conductive device comprises a fixing element for fixing to the electrodes, a contact element for electric connection, and a connection element connecting the fixing element and the contact part.

The present invention further provides a method for manufacturing a GI tract positioning switch according to any one of the above embodiments, comprising the following steps: disposing a first electrode and a second electrode on a base and spacing the first electrode and the second electrode apart; electrically connecting a conductive device to the first electrode and the second electrode respectively; and forming a positioning film on the first electrode and the second electrode to cover the first electrode and the second electrode.

The present invention further provides a site-specific delivery capsule (SSDC), comprising an enclosure and drug delivery or/and sampling device arranged inside the enclosure. A GI tract positioning switch according to any one of the above embodiments is fixed to the enclosure, and the conductive device in the switch is electrically connected to the conductive device in the drug delivery or/and sampling device.

In one preferred embodiment, the GI tract positioning switch is disposed on the enclosure of the SSDC.

The GI tract positioning switch disclosed herein comprises a base, a first electrode, a second electrode, a conductive device and a positioning film. The first electrode and the second electrode are spaced apart from each other, fixed on the base and electrically connected to the conductive device respectively. Both the first electrode and second electrode are insert electrode and covered by the positioning film. When the positioning film reaches the environment required for dissolution or/and degradation, it dissolves or/and degrades so that the electrodes are exposed, and the exposed electrodes contact the digestive juice to form a loop to trigger the drug delivery or/and sampling function of SSDC. Therefore, selection of the positioning film can accurately control the GI tract positioning switch to be turned on at different regions of the gastrointestinal tract, thereby triggering the drug delivery or/and sampling function of SSDC. In this way, a large external instrument is not needed for positioning in GI tract. Therefore, SSDC becomes simple in operation and use, and realizes independent delivery of drug for patients. Moreover, the GI tract positioning switch not only saves the space inside the capsule, provides ample space for drug delivery or/and sampling, but also reduces the cost of SSDC.

BRIEF DESCRIPTION OF THE DRAWINGS

In order to describe the technical solutions in the embodiments of the present invention more clearly, the drawings used in the description of embodiments are briefly introduced below. Obviously, the drawings just show some embodiments of the present invention. For those having ordinary skill in the art, other drawings can be obtained according to these drawings, without creative work.

DETAILED DESCRIPTION

The present invention can be described in detail below with reference to the accompanying drawings and preferred embodiments. However, the embodiments are not intended to limit the invention, and obviously, the described embodiments are only an element of the embodiments of the present invention, but not all of them. All other embodiments obtained by those having ordinary skill in the art without creative work based on the embodiments of the present invention are included in the scope of the present invention.

The present invention provides a gastrointestinal (GI) tract positioning switch 100, a manufacture method of the GI tract positioning switch 100 and a site-specific delivery capsule 200. The GI tract positioning switch 100 is disposed on the enclosure of the site-specific delivery capsule 200.

Figure 1:
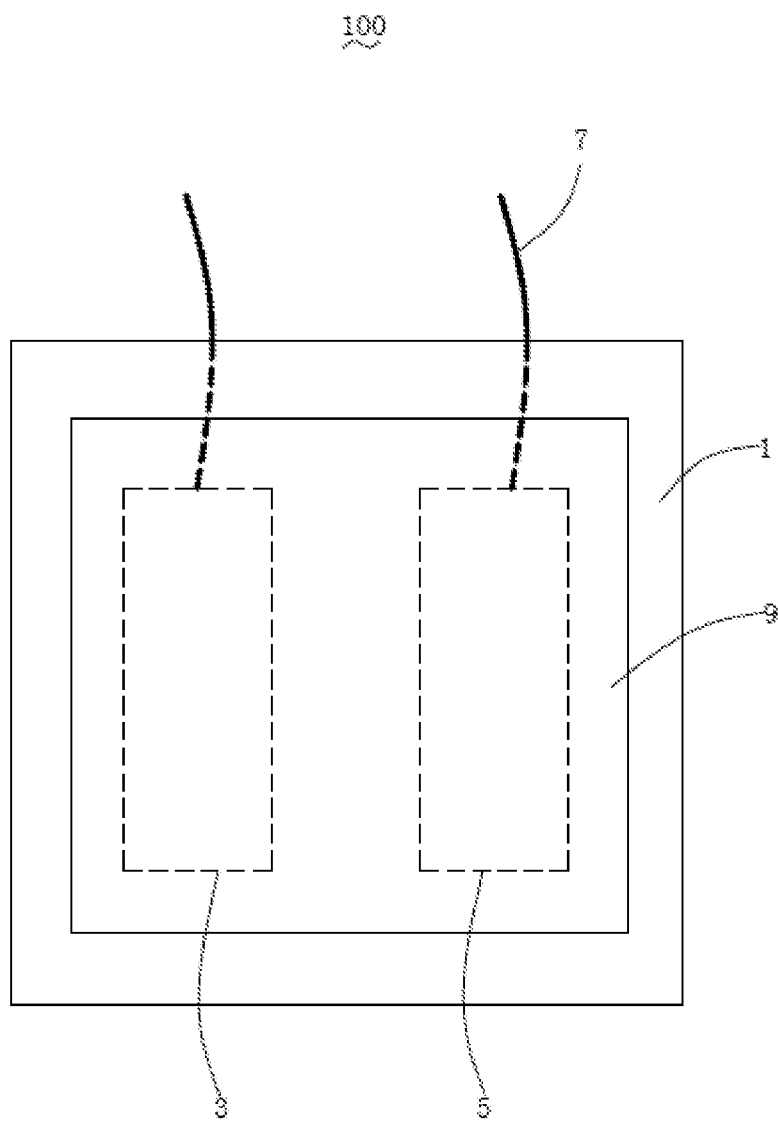
FIG. 1 is a structural view showing one preferred embodiment of a GI tract positioning switch according to the present invention.
Figure 2:
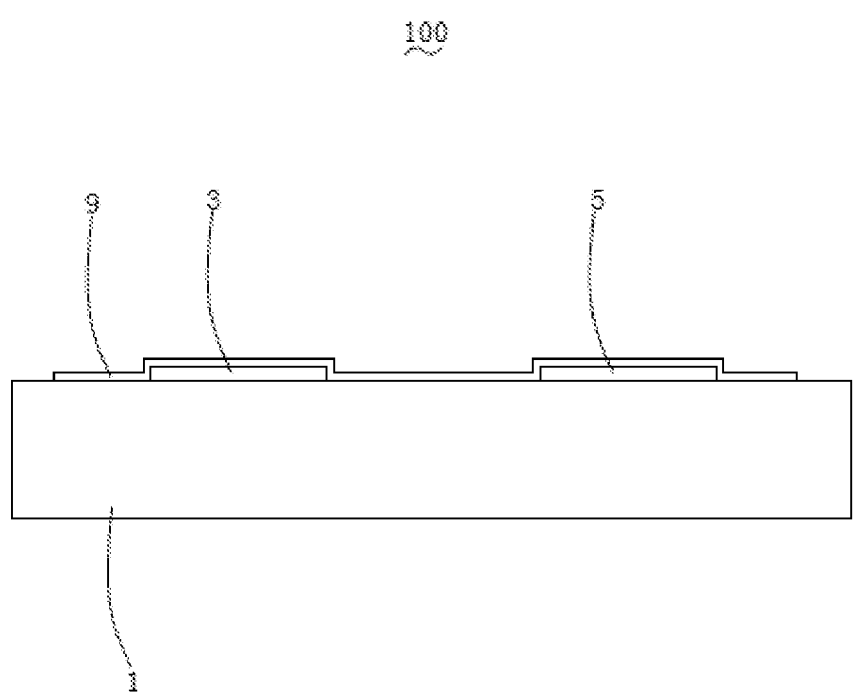
FIG. 2 is a structural view at another angle of FIG. 1 showing one preferred embodiment of a GI tract positioning switch according to the present invention.

Referring to FIG. 1 and FIG. 2, the GI tract positioning switch 100 comprises a base 1, a first electrode 3, a second electrode 5, a conductive device 7 and a positioning film 9. The first electrode 3 and the second electrode 5 are spaced apart from each other, and fixed on the base 1. The first electrode 3 and the second electrode 5 are electrically connected to a conductive device 7 respectively, and covered by the positioning film 9. Both the first electrode 3 and the second electrode 5 are an inert electrode, and can be exposed after dissolution or/and degradation of the positioning film 9 in the stomach or intestine. The exposed first electrode 3 and the second electrode 5 are in contact with the digestive juice in the stomach or intestine to form a circuit.

The base 1 is made of a material with good biocompatibility. For example, the material is acrylonitrile-butadiene-styrene copolymer (also known as ABS resin). The first electrode 3 or/and the second electrode 5 can be an inert electrode made of an inert conductive metal, such as gold, platinum and silver, or an inert electrode made of inert non-metal substance, such as a carbon electrode. The conductive device 7 comprises a fixing element for fixing to the electrodes, a contact element for electric connection, and a connection element connecting the fixing element and the contact element. For example, the conductive device 7 is a wire or a conductive slip ring. The contact element of the conductive device 7 is electrically connected to a unit of the site-specific delivery capsule 200. For example, the contact element is electrically connected to a processer of the site-specific delivery capsule 200.

The shape of the first electrode 3 or/and the second electrode 5 can be, but is not limited to, a rectangle, a square, a circle, a cross, an arrow, a flower, a gammadion, or a multi-finger cross.

When the inert electrode is made of an inert conductive metal, the conductive device 7 can be welded to the inert electrode or bonded to the inert electrode by a conductive adhesive. When the inert electrode is made of a non-metal, the conductive device 7 is bonded to the inert electrode by a conductive adhesive.

In the embodiment, both the first electrode 3 and the second electrode 5 are an inert electrode made of inert conductive metal. The first electrode 3 and the second electrode 5 can be welded to the conductive device 7 respectively, or the first electrode 3 and the second electrode 5 can be bonded to the conductive device 7 by a conductive adhesive respectively, or one of the first electrode 3 and the second electrode 5 is bonded to the conductive device 7 by a conductive adhesive while the other is welded to the conductive device 7. In the embodiment, the first electrode 3 and the second electrode 5 are electrically connected to the conductive device 7 in the same manner.

Further, the first electrode 3 and the second electrode 5 are formed by applying an inert conductive metal coating on the base 1 through sputtering coating process.

In a further preferred embodiment, the first electrode 3 and the second electrode 5 are formed by applying an inert conductive metal coating on the base 1 through magnetron sputtering coating process.

Since different regions of the human gastrointestinal tract have special physiological parameters, such as pH value and the number of microbes, some polymer materials can dissolve or/and degrade in different pH environments, and natural polysaccharides can degrade under the action of intestinal flora. Therefore, the positioning film 9 is made of a material that can dissolve or/and degrade in the stomach or intestine, so that the positioning film 9 can dissolve or/and degrade in the stomach or intestine.

Film-forming materials of the positioning film 9 can be selected from the following two types.

The film-forming materials of the positioning film 9 can be acrylic resin for pharmaceutical excipients. The acrylic resin, which refers to a kind of macromolecular compound created by mass polymerization of acrylic acid (or methacrylic acid and their esters such as methyl ester, ethyl ester, etc.), or by co-polymerization of acrylic acid and methacrylic acid (or their esters such as methyl ester, ethyl ester, dimethyl amino ethyl ester, etc.) by two monomers (binary) or three monomers (ternary) according to a certain ratio. This kind of compound does not degrade in human body, and is safe and non-toxic. Due to its structural characteristics, the drug can be designed to dissolve in the stomach or intestine as expected, and can be made into a targeted drug delivery system. For example, the film-forming materials of the positioning film 9 can be a copolymer of butyl methacrylate, dimethyl aminoethyl methacrylate, and methyl methacrylate (1:2:1), which can dissolve quickly in media with a pH less than 5, and has good film-forming property. For example, the film-forming materials of the positioning film 9 can be a copolymer of methacrylic acid and methyl methacrylate (1:1), which can dissolve in a solution with a pH greater than 6, and has good film forming property. For example, the film-forming materials of the positioning film 9 can be a copolymer of methacrylic acid and methyl methacrylate (1:2), which can dissolve in a solution with a pH greater than 7, and has good film-forming property.

The film-forming materials of the positioning film 9 can be natural polysaccharides, such as chitosan, pectin, guar gum, etc. The natural polysaccharides can be degraded by microorganisms in specific colon sites and have good film-forming properties.

The positioning film 9 is formed by coating film-forming materials on the first electrode 3 and the second electrode 5 by a spray coating method or a dip coating method. In this way, the first electrode 3 and the second electrode 5 can be completely isolated from the outside in a non-gastrointestinal environment or a simulated gastrointestinal environment.

Figure 3:
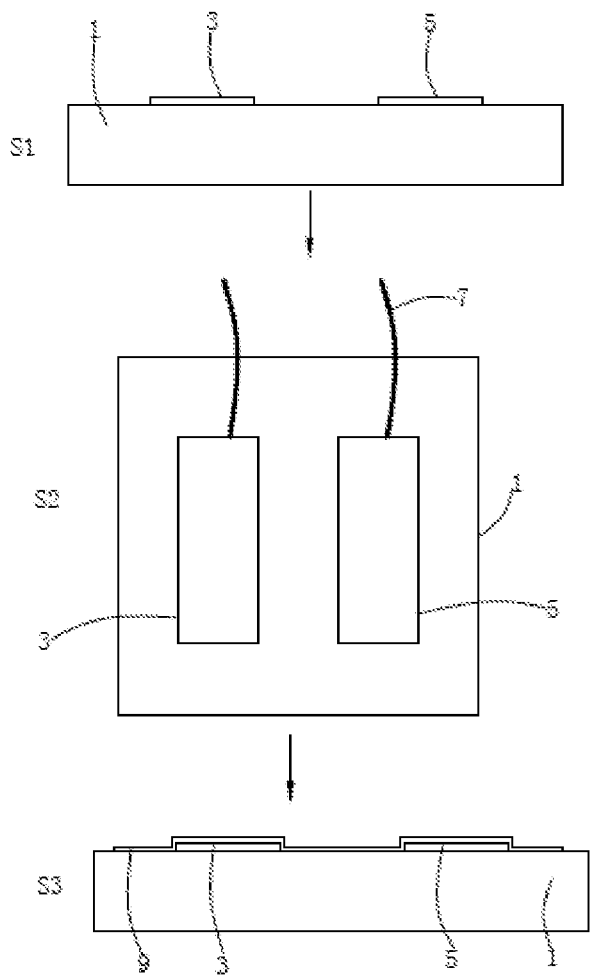
FIG. 3 is a flow diagram showing the manufacture method of a GI tract positioning switch as shown in FIG. 1.

Referring to FIG. 3, the present invention further provides a method of manufacturing the GI tract positioning switch, comprising the following steps.

Step S1: a first electrode 3 and a second electrode 5 are disposed on a base 1 and spacing the first electrode 3 and the second electrode 5 apart. In the embodiment, the first electrode 3 and the second electrode 5 are formed on the base 1 by applying an inert conductive metal (such as gold, platinum, silver, etc.) coating through sputtering coating process. In a further preferred embodiment, the first electrode 3 and the second electrode 5 are formed on the base 1 by applying an inert conductive metal (such as gold, platinum, silver, etc.) coating through magnetron sputtering coating process.

Step S2: a conductive device 7 is electrically connected to the first electrode 3 and the second electrode 5 respectively. In the embodiment, the first electrode 3 and the second electrode 5 can be welded to the conductive device 7 respectively, or the first electrode 3 and the second electrode 5 can be bonded to the conductive device 7 by a conductive adhesive respectively, or one of the first electrode 3 and the second electrode 5 is bonded to the conductive device 7 by a conductive adhesive while the other is welded to the conductive device 7.

Step S3: a positioning film 9 is formed on the first electrode 3 and the second electrode 5 to cover the first electrode 3 and the second electrode 5. In the embodiment, the positioning film 9 is formed by coating film-forming materials on the first electrode 3 and the second electrode 5 by a spray coating method or a dip coating method.

Figure 4:
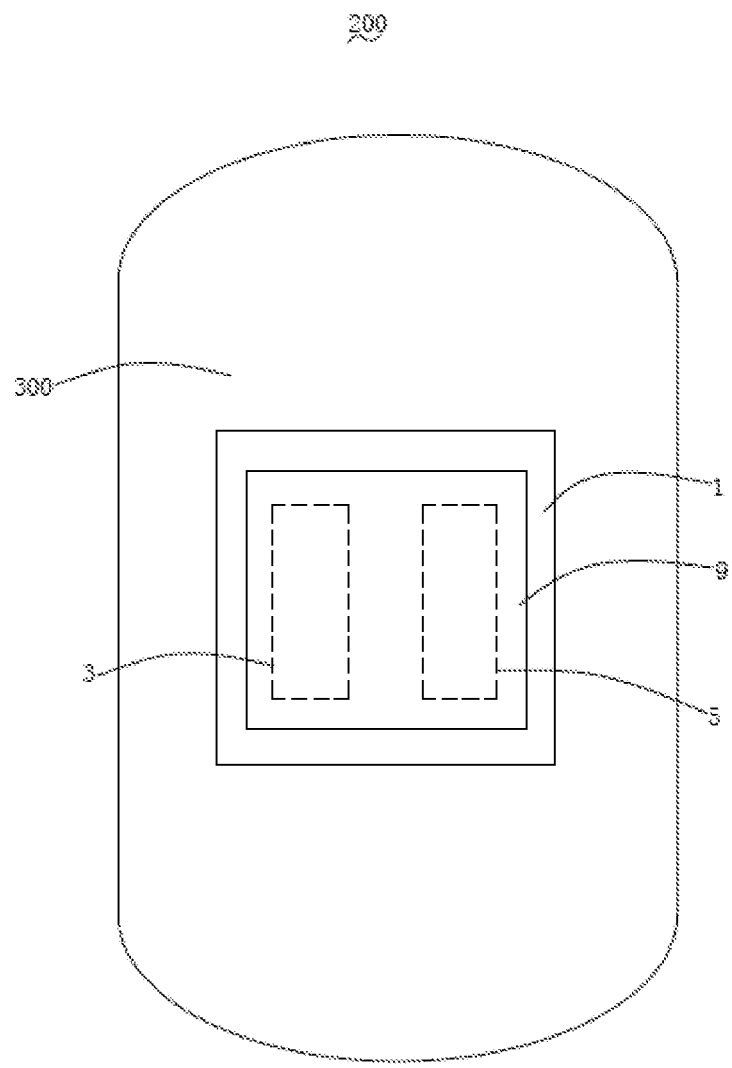
FIG. 4 is a structural view showing one preferred embodiment of a site-specific delivery capsule according to the present invention.

The present invention further provides a site-specific delivery capsule 200, as shown in FIG. 4. The site-specific delivery capsule 200 comprises an enclosure 300 and drug delivery or/and sampling device arranged inside the enclosure 300 (not shown in FIG. 4). A GI tract positioning switch 100 is fixed onto the enclosure, and the conductive device 7 in the GI tract positioning switch 100 is electrically connected to the drug delivery or/and sampling device. For example, the conductive device 7 in the GI tract positioning switch 100 is electrically connected to a processor of the drug delivery or/and sampling device.

After a patient orally takes the site-specific delivery capsule 200 equipped with the GI tract positioning switch 100, the positioning film 9 of the GI tract positioning switch 100 is in full contact with the liquid in GI tract. After reaching a site where the conditions required for dissolution or/and degradation are met, the positioning film 9 dissolves or/and degrades, making the first electrode 3 and the second electrode 5 exposed to digestive juice. The first electrode 3 and second electrode 5 have a contact with the digestive juice to form a loop, so that the circuit of the drug delivery or/and sampling device is closed, and the drug delivery or/and sampling function is triggered. Therefore, selection of the positioning film 9 can accurately control the GI tract positioning switch to be turned on at different regions of the gastrointestinal tract, thereby triggering the drug delivery or/and sampling function of SSDC. In this way, a large external instrument is not needed for positioning in GI tract. Therefore, SSDC becomes simple in operation and use, and realizes independent delivery of drug for patients. Moreover, the GI tract positioning switch 100 not only saves the space inside the capsule, provides ample space for drug delivery or/and sampling, but also reduces the cost of SSDC.

For example, the positioning film made of a copolymer of butyl methacrylate, dimethyl aminoethyl methacrylate, and methyl methacrylate (1:2:1) dissolves after reaching the stomach, so that the internal circuit of the site-specific delivery capsule is closed, to trigger drug delivery. For example, the positioning film made of a copolymer of methacrylic acid and ethyl acrylate (1:1) dissolves after reaching the small intestine to trigger drug delivery. For example, the positioning film made of natural polysaccharides (chitosan, pectin, guar gum, etc.) degrades after reaching the colon to trigger drug delivery. For example, the positioning film made of a copolymer of methacrylic acid, methyl acrylate, and methyl methacrylate (1:1:1) dissolves after reaching the colon to trigger drug delivery.

In the embodiment, the GI tract positioning switch 100 is disposed on the enclosure of the SSDC.

The GI tract positioning switch 100 disclosed herein comprises a base 1, a first electrode 3, a second electrode 5, a conductive device 7 and a positioning film 9. The first electrode 3 and the second electrode 5 are spaced apart from each other, fixed on the base 1 and electrically connected to the conductive device 7 respectively. Both the first electrode 3 and second electrode 5 are insert electrode and covered by the positioning film 9. When the positioning film 9 reaches the environment required for dissolution or/and degradation, it dissolves or/and degrades so that the electrodes are exposed, and the exposed electrodes contact the digestive juice to form a loop to trigger the drug delivery or/and sampling function of SSDC. Therefore, selection of the positioning film can accurately control the GI tract positioning switch to be turned on at different regions of the gastrointestinal tract, thereby triggering the drug delivery or/and sampling function of SSDC. In this way, a large external instrument is not needed for positioning in GI tract. Therefore, SSDC becomes simple in operation and use, and realizes independent delivery of drug for patients. Moreover, the GI tract positioning switch not only saves the space inside the capsule, provides ample space for drug delivery or/and sampling, but also reduces the cost of SSDC.

The embodiments shown and described above are only examples. Even though numerous characteristics and advantages of the present technology have been set forth in the foregoing description, together with details of the structure and function of the present disclosure, the disclosure is illustrative only, and changes may be made in the detail, including in particular the matters of shape, size and arrangement of parts within the principles of the present disclosure, up to and including the full extent established by the broad general meaning of the terms used in the claims.

What is claimed is:

1. A gastrointestinal tract positioning switch, comprising:
   a base, a first electrode, a second electrode, a conductive device and a positioning film, wherein
   the first electrode and the second electrode are spaced apart from each other and fixed on the base, and said base is directly disposed on along a length of an enclosure of a site-specific delivery capsule;
   the first electrode and the second electrode are electrically connected to the conductive device respectively and both the first electrode and second electrode, and partial base at a uniform thickness, are directly covered by the positioning film;
   both the first electrode and the second electrode are inert electrodes, and are exposed after dissolution or/and degradation of the positioning film in a stomach or intestine, wherein the conductive device comprises a contact element, configured to be electrically connected to a unit of the site-specific delivery capsule, thereby triggering a drug delivery or/and sampling function of the site-specific delivery capsule, wherein the base is made of an acrylonitrile-butadiene-styrene copolymer.

2. The gastrointestinal tract positioning switch of claim 1, wherein both the first electrode and the second electrode are made of inert conductive metal.

3. The gastrointestinal tract positioning switch of claim 2, wherein the first electrode and the second electrode are formed by applying an inert conductive metal coating on the base through a sputtering coating process.

4. The gastrointestinal tract positioning switch of claim 2, wherein the conductive device is welded to the first electrode and the second electrode.

5. The gastrointestinal tract positioning switch of claim 1, wherein the conductive device is bonded to the first electrode and the second electrode through conductive adhesive.

6. The gastrointestinal tract positioning switch of claim 1, wherein the positioning film is formed on the first electrode and the second electrode by coating film-forming materials, a spray coating method or a dip coating method.

7. The gastrointestinal tract positioning switch of claim 1, wherein the conductive device further comprises a fixing element for fixing to the electrodes, the contact element for electrical connection, and a connection element connecting the fixing element and the contact element.

8. The gastrointestinal tract positioning switch of claim 1, wherein the unit of the site-specific delivery capsule, is a contact device of a drug delivery device or/sampling device.

9. The gastrointestinal tract positioning switch of claim 1, wherein the unit of the site-specific delivery capsule is a processor.

10. A method of manufacturing the gastrointestinal tract positioning switch of claim 1, comprising:
    disposing the first electrode and the second electrode on the base and spacing the first electrode and the second electrode apart;
    electrically connecting the conductive device to the first electrode and the second electrode respectively; and
    forming a positioning film, at a uniform thickness through spray coating or dip coating directly on the first electrode, the second electrode, and the base on the enclosure the site-specific delivery capsule.

* * * * *